United States Patent [19]

Pardridge

[11] Patent Number: 4,801,575
[45] Date of Patent: Jan. 31, 1989

[54] CHIMERIC PEPTIDES FOR NEUROPEPTIDE DELIVERY THROUGH THE BLOOD-BRAIN BARRIER

[75] Inventor: William M. Pardridge, Van Nuys, Calif.

[73] Assignee: The Regents of the University of California, Berkeley, Calif.

[21] Appl. No.: 891,867

[22] Filed: Jul. 30, 1986

[51] Int. Cl.$^4$ .................. A61K 37/02; C07K 17/00; C07K 7/40
[52] U.S. Cl. ...................................... 514/4; 424/85.7; 514/2; 514/3; 530/303; 530/311; 530/302; 530/351
[58] Field of Search .................. 424/85; 514/2, 3.4; 530/395, 303, 302, 350, 362, 351, 311, 315, 323, 402

[56] References Cited

U.S. PATENT DOCUMENTS 4,348,387 9/1982 Brownlee et al. .................. 424/178
4,522,750 6/1985 Ades et al. .......................... 530/395

FOREIGN PATENT DOCUMENTS 1564666 4/1980 United Kingdom .
2116979 10/1983 United Kingdom .

OTHER PUBLICATIONS

Carlson et al., Biochem. J., vol. 173, pp. 723-737, 1978.
Chemical Abstracts, vol. 102, Abstract No. 105874r, 1985.
Chemical Abstracts, vol. 92, Abstract No. 92580q, 1980.
Ito et al., Molecular and Cellular Endocrinology, vol. 36, pp. 165-173, 1984.
Yoshimosa et al, Diabetes, vol. 33, pp. 1051-1054, 1984.
Pardridge et al, Neuroendocrine Perspectives, vol. 2, pp. 107-121, 1983.
Interferon—A Conjugation to Human Osteogenic Sarcoma Monoclonal Antibody 791T/36., Pelham, Julie M.; Gray, J. D.; Flannery, G. R.; Pimm. M. V.; Baldwin, R. W. (Cancer Res. Campaign Lab., Univ. Nottingham, Nottingham, UK, Cancer Immunochemistry, vol. 100,4584z, 1984.
"Conjugation of Poly-L-Lysine to Albumin and Horseradish Peroxidase: A Novel Method of Enhancing the Cellular Uptake of Proteins", Proc. Natl. Acad. Sci., USA, vol. 75, No. 4, pp. 1872-1876, Apr. 1978, Cell Biology.
"Insulin: Carrier Potential for Enzyme and Drug Therapy", Science, vol. 223, 23 Mar. 1984, pp. 1304-1306.
"Strategies for Drug Delivery Through the Blood-Brain Barrier", from: Directaed Drug Delivery, edited by: Ronald T. Borchardt, Arnold J. Repta, and Valentino J. Stella, the Humana Press. 1985, pp. 83-96.
Chapter 31. Strategies for Delivery of Drugs Through the Blood-Brain Barrier, Annual Reports in Medicinal Chemistry-20, Sep. 1985, Academic Press, Inc., pp. 305-313.
"Rapid Sequestration and Degradation of Somatostatin Analogues by Isolated Brain Microvessels", Journal of Neurochemistry, Raven Press, New York, copyrighted 1985, International Society for Neurochemistry, pp. 1178'4 1184, vol. 44, No. 4, 1985.
"Human Blood-Brain Barrier Insulin Receptor", Journal of Neurochemistry, Raven Press, New York, copyrighted 1985, International Society for Neurochemistry, 8 pages.

Primary Examiner—Blondel Hazel
Attorney, Agent, or Firm—Poms, Smith, Lande & Rose

[57] ABSTRACT

Chimeric peptides adapted for delivering neuropharmaceutical agents, such as neuropeptides into the brain by receptor-mediated transcytosis through the blood-brain barrier. The chimeric peptides include a peptide which by itself is capable of crossing the blood-brain barrier by transcytosis at a relatively high rate. The transportable peptide is conjugated to a hydrophilic neuropeptide which by itself is transportable only at a very low rate into the brain across the blood-brain barrier. The resulting chimeric peptide is transported into the brain at a much higher rate than the neuropeptide alone to thereby provide an effective means for introducing hydrophilic neuropeptides into the brain through the blood-brain barrier.

19 Claims, 1 Drawing Sheet

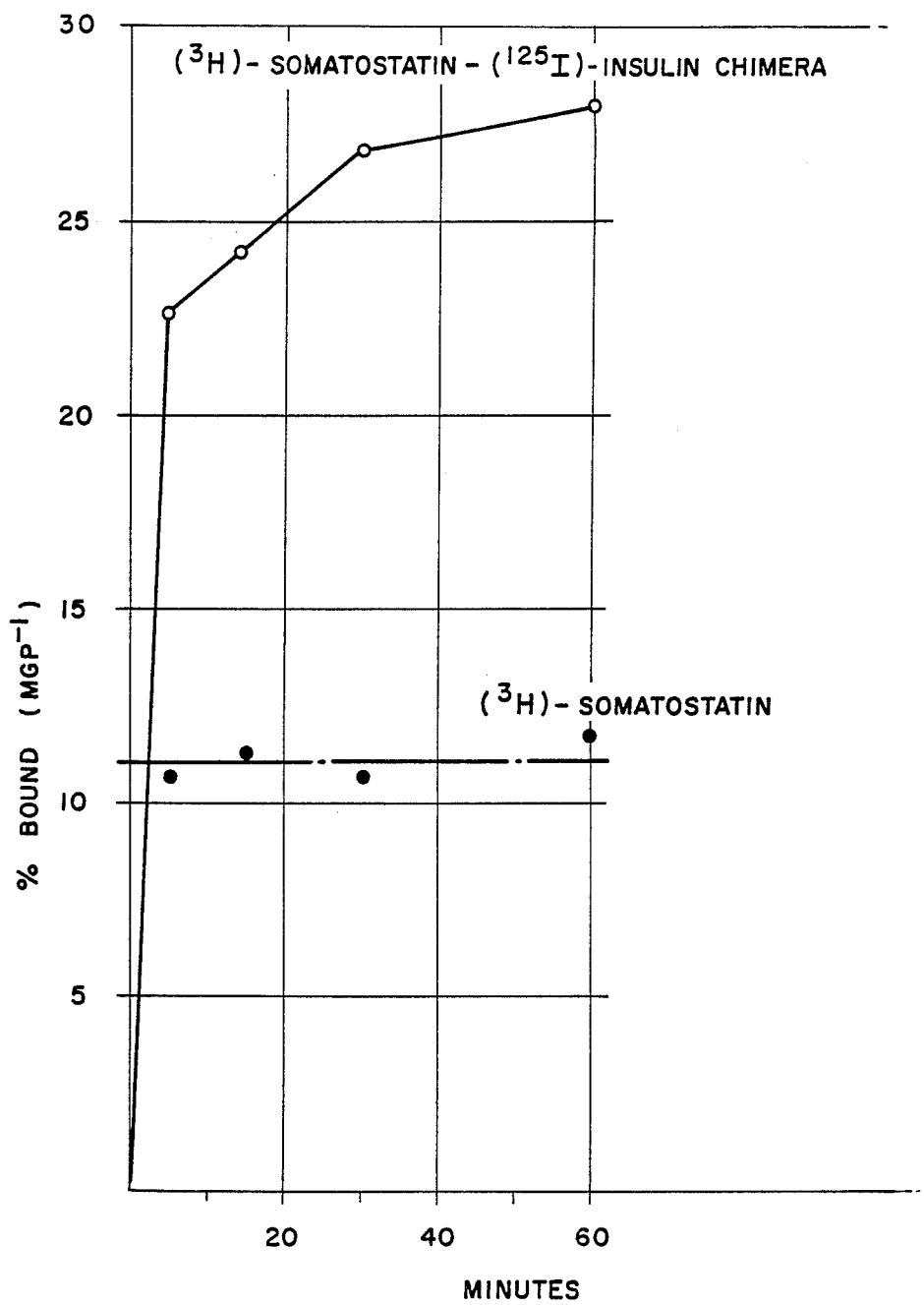

CHIMERIC PEPTIDES FOR NEUROPEPTIDE DELIVERY THROUGH THE BLOOD-BRAIN BARRIER

This invention was made with Government support under Grant No. NS-17701 awarded by the National Institutes of Health. The Government has certain rights in this invention.

BACKGROUND OF THE INVENTION

The present invention relates generally to the introduction of neuropharmaceutical agents into the brain by transcytosis across the blood-brain barrier. More particularly, the present invention relates to chimeric peptides which are capable of transporting neuropharmaceutical agents into the brain by receptor-mediated transcytosis across the blood-brain barrier.

The vertebrate brain has a unique capillary system which is unlike that in any other organ in the body. The unique capillary system has morphologic characteristics which make up the blood-brain barrier (BBB). The blood-brain barrier acts as a systemwide cellular membrane which separates the brain interstitial space from the blood.

The unique morphologic characteristics of the brain capillaries which make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry are very low.

Various strategies have been developed for introducing those drugs into the brain which otherwise would not cross the blood-brain barrier. The most widely used strategies involve invasive procedures where the drug is delivered directly into the brain. The most common procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain.

Although invasive procedures for the direct delivery of drugs to the brain ventricles have experienced some success, they have not been entirely successful because they only distribute the drug to superficial areas of the brain tissues, and not to the structures deep within the brain. Further, the invasive procedures are potentially harmful to the patient.

Other approaches to circumventing the blood-brain barrier utilize pharmacolgic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily transported across the blood-brain barrier. Although the pharmacolgic approaches have been used with some success, they may not be entirely satisfactory for delivery of peptides through the BBB based on the inventor's experience with cyclosporin transpsort through the BBB. Cyclosporin is a highly latentiated (lipid-soluble) peptide that crosses the BBB relatively slowly.

Another approach to circumventing the blood-brain barrier involves the intra-arterial infusion of hypertonic substances which transiently open the blood-brain barrier to allow passage of hydrophilic drugs. However, hypertonic substances are potentially toxic and may damage the blood-brain barrier.

There presently is a need to provide improved substances and methods for delivering hydrophilic drugs and peptides across the blood-brain barrier and into the brain. It is desirable that such improved substances and methods provide for uniform introduction of the hydrophilic peptide or drug throughout the brain and present as little risk to the patient as possible.

SUMMARY OF THE INVENTION

In accordance with the present invention, new procedures and substances are disclosed which provide uniform distribution of neuropeptides and other drugs throughout the brain while reducing the problems inherent in prior invasive and pharmacologic drug introduction procedures.

The present invention is based on the surprising discovery that hydrophilic peptides may be physiologically transported across the blood-brain barrier by coupling or conjugating the drug to a transportable peptide which is capable of crossing the blood-brain barrier by receptor-mediated transcytosis. This discovery is particularly surprising in view of the traditional notion that the blood-brain barrier is a passive barrier which is impenetrable by hydrophilic drugs or peptides.

The invention involves novel chimeric peptides which are adapted to deliver a neuropharmaceutical agent into the brain by transcytosis across the blood-brain barrier. The chimeric peptides include a transportable peptide that is capable of crossing the blood-brain barrier at relatively high rate by receptor-mediated transcytosis. The transportable peptide is conjugated with a neuropharmaceutical agent to form the chimeric peptide. The neuropharmaceutical agent is generally a hydrophilic peptide that does not by itself significantly cross the BBB. The conjugation of transportable peptides with neuropharmaceutical agents was surprisingly found to produce chimeric peptides which were capable of being transported across the blood-brain barrier.

As a feature of the present invention, the chimeric peptides are believed to be transported across the blood-brain barrier by the physiologic process of transcytosis via receptors in the blood-brain barrier. This insures that the chimeric peptide is distributed uniformly to all parts of the brain. In addition, the introduction of the chimeric peptide into the brain by a physiologic pathway reduces the harmful side effects and risks inherent in the traditional invasive and pharmacological approaches.

The present invention also includes methods for administering the chimeric peptides subcutaneously or intranasally and the chimeric peptide containing compositions utilized in such methods of treatment.

The above-discussed and many other features and attendant advantages of the present invention will become apparent as the invention becomes better understood by reference to the following detailed description when considered in conjunction with the accompanying drawing.

BRIEF DESCRIPTION OF THE DRAWING

The FIGURE is a chart showing the results of the tests described in Example No. 2.

DETAILED DESCRIPTION OF THE INVENTION

The chimeric peptides in accordance with the present invention are useful in delivering a wide variety of neuropharmaceutical agents to the brain. The invention is particularly well suited for delivering neuropharmaceutical agents which are hydrophilic peptides. These hydrophilic peptides are generally not transported across the blood-brain barrier to any significant degree.

Exemplary hydrophilic peptide neuropharmaceutical agents are: thyrotropin releasing hormone (TRH)—used to treat spinal cord injury and Lou Gehrig's disease; vasopressin—used to treat amnesia; alpha interferon—used to treat multiple sclerosis; somatostatin—used to treat Alzheimer's disease; endorphin—used to treat pain; L-methionyl (sulfone)-L-glutamyl-L-histidyl-L-phenylalanyl-D-lysyl-L-phenylalanine (an analogue of adrenocorticotrophic hormone (ACTH)-4-9)—used to treat epilepsy; and muramyl dipeptide—used to treat insomnia. All of these neuropharmaceutical peptides are available commercially or they may be isolated from natural sources by well-known techniques.

The following description will be limited to chimeric peptides in which the neuropharmaceutical agents are hydrophilic peptides (neuropeptides) with it being understood that the invention has application to any neuropharmaceutical agent which by itself is transported at a low or non-existent rate across the blood-brain barrier. The invention also has application where it is desired to increase the rate at which the neuropharmaceutical agent is transported across the blood-brain barrier.

The chimeric peptide includes the hydrophilic peptide drug conjugated to a transportable peptide which is capable of crossing the blood-brain barrier by transcytosis at a much higher rate than the hydrophilic neuropeptides. Suitable transportable peptides include: insulin, transferrin, insulin-like growth factor I (IGF-I), insulin-like growth factor II (IGF-II), basic albumin and prolactin.

Transferrin is an 80K glycoprotein that is the principal iron transport protein in the circulation. Transferrin is also a protein that is enriched in the cerebrospinal fluid (CSF). Transferrin is widely available and may be purchased or isolated from blood or CSF by well-known procedures.

Insulin, IGF-I and IGF-II are also commonly available. Insulin is available on a wide scale commercially and may also be recovered from natural sources by well-known techniques. IGF-I and IGF-II are available from commercial outlets such as Amgen or Peninsula Labs or they may be isolated from natural sources according to the procedure of Rosenfeld et al. (J. Clin Endocrinol. Metab. 55, 434, 1982).

Basic albumin or cationized albumin has a isoelectric point (pI) of 8.5 as compared to a pI of 3.9 for natural albumin. Cationized albumin, unlike natural albumin, enters the brain rapidly across the blood-brain barrier. Cationized albumin (pI=8.5) is prepared preferably by covalent coupling of hexamethylene-diamine (HMD) to bovine serum albumin (pI=3.5) according to Bergmann, et al., "Cationized Serum Albumin Enhances Response of Cultured Fetal Rat Long Bones To Parathyroid Hormone", *Endocrinology*, 116: 1729-1733 (1985). An exemplary synthesis is as follows: 10 ml of a 10% solution of albumin in water is slowly added to 60 ml of 2.0M HMD and the pH of the solution is adjusted to 6-7 with 1N HCl. After 30 minutes, 1 g of N-ethyl-N'-3-(dimethylaminopropyl)carbodiimide hydrochloride (EDAC) is added to activate the carboxyl groups of the albumin, followed by the addition of another 1 g EDAC 1 hour later. The pH is constantly adjusted to 6-7 with 0.2N HCl. The solution is allowed to stand overnight with constant stirring. The next day the solution is dialyzed extensively against distilled water. This solution is then purified by chromatofocusing using the Pharmacia polybuffer exchanger 94 resin and the polybuffer 96 elution buffer.

Prolactin is a hormone which is secreted by the anterior pituitary. Prolactin is widely available commercially or it can be isolated from pituitary glands by well-known procedures.

The chimeric peptides are made by conjugating a transportable peptide with the neuropharmaceutical peptide.

The conjugation may be carried out using bifunctional reagents which are capable of reacting with each of the peptides and forming a bridge between the two. The preferred method of conjugation involves peptide thiolation wherein the two peptides are treated with a reagent such as N-Succinimidyl 3-(2-pyridyldithio)propionate (SPDP) to form a disulfide bridge between the two peptides to form the chimeric peptide. Other known conjugation agents may be used, so long as they provide linkage of the two peptides (i.e. the hydrophilic peptide drug and the transportable peptide) together without denaturing them. Preferably, the linkage can be easily broken once the chimeric peptide has entered the brain. Suitable examples of conjugation reagents include: glutaraldehyde and cystamine and EDAC. Conjugation of peptides using glutaraldehyde is described in Poznansky et al., Insulin: Carrier potential for enzyme and drug therapy. *Science* 223: 1304-1306, 1984. Conjugation of peptides using cystamine and EDAC is described in Ito et al., Transmembrane delivery of polypeptide hormones bypassing the intrinsic cell surface receptors: a conjugate of insulin with a2-macroglobulin (a2M) recognizing both insulin and a2M receptors and its biological activity in relation to endocytic pathways. *Mol Cell Endocrinol* 36: 165, 1984.

Examples of preferred chimeric peptides include those having the general structure

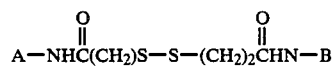

where A is somatostatin, thyrotropin releasing hormone (TRH), vasopressin, alpha interferon, endorphin, muramyl dipeptide or ACTH 4-9 analogue; and B is insulin, IGF-I, IGF-II, transferrin, cationized (basic) albumin or prolactin.

Other examples of preferred chimeric peptides include those listed above wherein the disulfide conjugating bridge between A and B is replaced with bridges having the following structures:

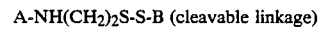

which are formed when cystamine and EDAC are employed as the bridge reagents;

A-NH=CH(CH₂)₃CH=NH-B (non-cleavable linkage)

which are formed when glutaraldehyde is employed as bridge reagent.

The chimeric peptides can be introduced into the body by any conventional procedure including parenteral injection or intranasal inhalation. Preferably, the chimeric peptides are combined with a compatible pharmaceutical carrier and injected parenterally or if desired combined with a suitable carrier and administered intranasally in accordance with the well-known conventional procedures used for intranasal administration of insulin. Suitable carrier solutions include those commonly used in injectable or nasal-inhaled hormone preparations such as sterile saline at a pH of around 5 which includes common bacteriostatic agents. The concentration of a chimeric peptide in the carrier will vary depending upon the specific transportable peptide and the specific neuropharmaceutical peptide. Preferably, levels of the chimeric peptide in the carrier should be between about 0.001 weight percent to 0.01 weight percent. As a general rule, the dosage levels and percent of chimeric peptides present in the injection or intranasal solution should correspond to the accepted and established dosages for the particular neuropharmaceutical peptide as well as the transportable peptide.

Examples of practice are as follows:

EXAMPLE 1

Synthesis of Somatostatin-Insulin Chimera

Somatostatin, a peptide deficient in the brain of Alzheimer's disease, is a peptide which is not transported through the blood-brain barrier. Conversely, insulin is a peptide that is transported through the blood-brain barrier. The transportability of insulin through the blood-brain barrier is set forth in my article entitled "Receptor-Mediated Peptide Transport Through The Blood-Brain Barrier" (Endocrine Reviews, Vol. 7, No. 3, August 1986), the contents of which is hereby incorporated by reference.

Somatostatin and insulin were conjugated by peptide thiolation using a reversible peptide-peptide conjugation method as described by Carlsson, et al. in "Protein Thiolation and Reversible Protein-Protein Conjugation" (Biochem. J. (1978) 173, 723–737). A heterobifunctional reagent, N-succinimidyl 3-(2-pyridyldithio)-propionate (SPDP), was used to couple a lysine or free N-terminus on insulin to a free lysine or amino terminus on somatostatin. Approximately 0.3 mg of insulin and 26 uCi of ¹²⁵I-insulin in 2 ml of phosphate buffered saline was prepared. To half of this was added 4 lambdas of 20 mM fresh SPDP and this was incubated at room temperature for 45 minutes.

Separately, 180 uCi of tritiated somatostatin in 180 uL of 0.01N HCl was solubilized and added to 180 uL of 0.2M phosphate buffered saline. To half of this, 4 uL of 20 mM SPDP was added and this was incubated for 45 minutes, followed by acidification with 20 uL of 0.75M sodium acetate (pH=4.5) followed by reduction with 20 uL of 0.25M dithiothreitol. This was incubated at room temperature for 30 minutes followed by brief dialysis to remove unreacted small molecules. The conjugated insulin and conjugated somatostatin were then incubated overnight at room temperature followed by dialysis and counting for tritium and ¹²⁵I radioactivity. This resulted in a total of 53 uCi of ³H-somatostatin coupled to 5.3 uCi of ¹²⁵I-insulin in 2 ml of phosphate buffered saline.

The structure of the somatostatin-insulin chimera is shown below.

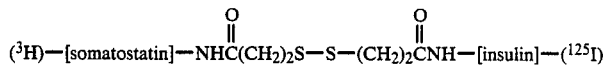

Somatostatin has the following amino acid sequence: Ala-Gly-Cys-Lys-Asn-Phe-Phe-Trp-Lys-Thr-Phe-Thr-Ser-Cys. Insulin is a double chain protein hormone whose structure is well known.

EXAMPLE 2

Radioreceptor Assay Using Isolated Bovine Brain Microvessels and ³H-Somatostatin-¹²⁵I-Insulin Chimera Somatostatin was obtained from Peninsula Laboratories and tritiated by reductive methylation using ³H-sodium borohydride. Insulin was obtained from Sigma Chemical Company and was iodinated by oxidative iodination using chloramine T and ¹²⁵I-iodine. The two compounds were coupled together using SPDP as described in Example 1. Bovine brain microvessels were isolated as described in Pardridge, et al., "Rapid Sequestration And Degradation Of Somatostatin Analogues By Isolated Brain Microvessels", (Journal of Neurochemistry, Vol. 44, No. 4, 1985, pp. 1178–1184).

³H-somatostatin was added to one set of microvessels for up to 60 minutes incubation at room temperature. In another set of incubations, the ³H-somatostatin-¹²⁵I-insulin chimera was also added. As shown in the figure, the uptake of the chimera was more than double that of the free somatostatin. Moreover, the uptake of the chimera increased with time, whereas there was no increase in time with the free somatostatin. The uptake of the free somatostatin likely represents nonspecific binding as described in the article mentioned above (Journal of Neurochemistry, Vol. 44, No. 4, 1985).

This example demonstrates the receptor-mediated transcytosis or endocytosis of somatostatin-insulin chimera via the insulin receptor. Previous studies have shown that the receptor-mediated endocytosis of peptides in the isolated brain microvessels is a reliable index of the in vivo blood-brain barrier receptor transport activity of peptides in vivo (see my previously-mentioned article in Endocrine Reviews, Vol. 7, No. 3, August 1986).

EXAMPLE 3

A chimeric peptide is prepared according to the same procedure as in Example 1 except that transferrin is substituted for insulin. The resulting chimeric peptide is combined with sterile saline to provide a solution containing 0.01 weight percent chimeric peptide which is administered to the patient parenterally or intranasally.

EXAMPLE 4

A chimeric peptide is prepared according to the same procedure as in Example 1 except that vasopressin is susbtituted for somatostatin. The resulting chimeric peptide is combined with sterile saline to provide a solution containing 0.01 weight percent chimeric peptide which is administered to the patient parenterally.

EXAMPLE 5

A chimeric peptide is prepared according to the same procedure as in Example 1 except that transferrin is coupled to alpha-interferon. The resulting chimeric peptide is combined with sterile saline to provide a solution containing 0.01 weight percent chimeric peptide which is administered to the patient or subject parenterally or intranasally.

EXAMPLE 6

A chimeric peptide is prepared according to the same procedure as in Example 1 except that IGF-II is coupled to beta-endorphin. The resulting chimeric peptide is combined with sterile saline to provide a solution containing 0.01 weight percent chimeric peptide which is administered to the patient or subject parenterally or intranasally.

EXAMPLE 7

A chimeric peptide is prepared according to the same procedure as in Example 1 except that insulin is coupled to ACTH 4-9 analogue. The resulting chimeric peptide is combined with sterile saline to provide a solution containing 0.01 weight percent chimeric peptide which is administered to the patient or subject parenterally or intranasally.

EXAMPLE 8

A chimeric peptide is prepared according to the same procedure as in Example 1 except that cationized albumin is coupled to hexosaminidase A. The resulting chimeric peptide is combined with sterile saline to provide a solution containing 0.01 weight percent chimeric peptide which is administered to the patient or subject parenterally or intranasally.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A chimeric peptide adapted for delivering a neuropharmaceutical agent into the brain by transcytosis through the blood-brain barrier, said chimeric peptide comprising:
    a transportable peptide capable of crossing the blood-brain barrier by transcytosis, said peptide being selected from the group consisting of insulin, transferrin, IGF-I, IGF-II, basic albumin and prolactin; and
    a neuropharmaceutical agent selected from the group consisting of somatostatin, thyrotropin releasing hormone, vasopressin, alpha interferon, endorphin, muramyl dipeptide and L-methionyl(sulfone)-L-glutamyl-L-histidyl-L-phenylalanyl-D-lysyl-L-phenylalanine, wherein said neuropharmaceutical agent is conjugated with said transportable peptide.

2. A chimeric peptide according to claim 1 wherein said transportable peptide and neuropharmaceutical agent are conjugated via a conjugation agent.

3. A chimeric peptide according to claim 2 wherein said conjugation agent is capable of conjugating the transportable peptide to said neuropharmaceutical agent by peptide thiolation or lysine coupling via glutaraldehyde.

4. A chimeric peptide according to claim 3 wherein said transportable peptide is insulin.

5. A chimeric peptide according to claim 4 wherein said neuropharmaceutical agent is somatostatin.

6. A chimeric peptide according to claim 1 having the formula

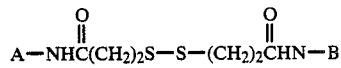

wherein A is said neuropharmaceutical agent and B is said transportable peptide.

7. A chimeric peptide according to claim 6 wherein A is somatostatin and B is insulin.

8. A composition comprising a chimeric peptide according to claim 1 and a pharmaceutically acceptable carrier for said chimeric peptide.

9. A composition according to claim 8 wherein said pharmaceutically acceptable carrier is sterile saline.

10. A method for delivering a neuropharmaceutical agent into the brain of an animal by transcytosis through the blood-brain barrier comprising the step of introducing a chimeric peptide into the bloodstream of said animal in a sufficient amount to provide transport of said chimeric peptide across said blood-brain barrier, wherein said chimeric peptide comprises a transportable peptide capable of crossing the blood-brain barrier conjugated with a neuropharmaceutical agent.

11. A method according to claim 10 wherein said chimeric peptide is introduced intra into the subject's bloodstream.

12. In a method for introducing a neuropharmaceutical agent into the brain across the blood-brain barrier, wherein the improvement comprises increasing the rate at which said neuropharmaceutical agent crosses the blood-brain barrier by conjugating said neuropharmaceutical agent with a transportable peptide capable of crossing the blood-brain carrier by transcytosis.

13. A method according to claim 10 wherein said transportable peptide is selected from the group consisting of insulin, transferrin, IGF-I, IGF-II, basic albumin and prolactin.

14. A method according to claim 10 wherein said neuropharmaceutical agent is a hydrophilic peptide.

15. A method according to claim 14 wherein said neuropharmaceutical agent is selected from the group consisting of somatostatin, thyrotropin releasing hormone, vasopressin, alpha interferon, endorphin, muramyl dipeptide and L-methionyl(sulfone)-L-glutamyl-L-histidyl-L-phenylalanyl-D-lysyl-L-phenylalanine.

16. A method according to claim 10 wherein said transportable peptide and neuropharmaceutical agent are conjugated via a conjugation agent.

17. A method according to claim 16 wherein said conjugation agent is capable of conjugating the transportable peptide to said neuropharmaceutical agent by peptide thiolation or lysine coupling via glutaraldehyde.

18. A method according to claim 17 wherein said transportable peptide is insulin.

19. A method according to claim 18 wherein said neuropharmaceutical agent is somatostatin.

* * * * *